US011266315B2

(12) United States Patent
Xia et al.

(10) Patent No.: US 11,266,315 B2
(45) Date of Patent: Mar. 8, 2022

(54) DEVICES AND METHODS FOR PHOTOACOUSTIC TOMOGRAPHY

(71) Applicant: The Research Foundation for The State University of New York, Amherst, NY (US)

(72) Inventors: Jun Xia, Amherst, NY (US); Yuehang Wang, Buffalo, NY (US)

(73) Assignee: The Research Foundation for The State University of New York, Amherst, NY (US)

( * ) Notice: Subject to any disclaimer, the term of this patent is extended or adjusted under 35 U.S.C. 154(b) by 484 days.

(21) Appl. No.: 15/781,329

(22) PCT Filed: Dec. 5, 2016

(86) PCT No.: PCT/US2016/065027
§ 371 (c)(1),
(2) Date: Jun. 4, 2018

(87) PCT Pub. No.: WO2017/096406
PCT Pub. Date: Jun. 8, 2017

(65) Prior Publication Data

US 2018/0317777 A1 Nov. 8, 2018

Related U.S. Application Data

(60) Provisional application No. 62/263,402, filed on Dec. 4, 2015.

(51) Int. Cl.
*A61B 5/00* (2006.01)
*G01N 21/17* (2006.01)
(Continued)

(52) U.S. Cl.
CPC .......... *A61B 5/0095* (2013.01); *A61B 5/0073* (2013.01); *G01N 21/1702* (2013.01);
(Continued)

(58) Field of Classification Search
None
See application file for complete search history.

(56) References Cited

U.S. PATENT DOCUMENTS 4,204,435 A * 5/1980 Bridoux .................. A61B 8/08 73/626
4,852,973 A * 8/1989 Durnin .............. G02B 27/0025 359/559

(Continued)

FOREIGN PATENT DOCUMENTS

JP S57161517 A 10/1982

OTHER PUBLICATIONS

Clement et al., "Ultrasound Field Measurement Using Binary Lens" IEEE Transactions on Ultrasonics, Ferroelectrics, and Frequency Control, vol. 62, No. 2, Feb. 2015 (Year: 2015).*

(Continued)

*Primary Examiner* — Colin T. Sakamoto
(74) *Attorney, Agent, or Firm* — Hodgson Russ LLP

(57) ABSTRACT

Devices and methods for photoacoustic tomography are disclosed herein. One exemplary photoacoustic tomography device uses a laser to produce acoustic waves in a sample. A transducer receives the acoustic waves through a slit formed by one or more blades positioned substantially parallel to the receiving aperture of the transducer. An acoustic absorber is affixed to each of the one or more blades along a surface proximal to the transducer. A processor acquires acoustic data and reconstructs photoacoustic tomographic images based on the acquired data. Reconstructing the image involves setting reconstruction parameters, defining a reconstruction area, reconstruction position, and pixel size, and calculating an acoustic travelling path for the sample to each transducer element. The acoustic travelling paths are saved into a three-dimensional array.

21 Claims, 5 Drawing Sheets

(51) Int. Cl.
*G01N 29/24* (2006.01)
*H04R 23/00* (2006.01)

(52) U.S. Cl.
CPC ......... *G01N 29/24* (2013.01); *G01N 29/2418* (2013.01); *H04R 23/008* (2013.01)

(56) References Cited

U.S. PATENT DOCUMENTS 4,887,885 A * 12/1989 Durnin ............... G02B 27/0025 359/559
5,535,751 A * 7/1996 Raz ..................... G01S 15/8925 600/459
9,226,666 B2 1/2016 Wang et al.
2002/0045819 A1* 4/2002 Garlick .............. G01N 29/0663 600/437
2002/0045830 A1* 4/2002 Powers ............... G01S 7/52025 600/459
2003/0012478 A1 1/2003 Pokrovski et al.
2005/0004458 A1* 1/2005 Kanayama ........... A61B 5/4312 600/437
2005/0187471 A1* 8/2005 Kanayama ........... A61B 5/0091 600/437
2006/0241472 A1* 10/2006 Osawa ..................... A61B 8/12 600/459
2007/0040469 A1* 2/2007 Yacoubian ............... H04N 5/30 310/311
2009/0149761 A1 6/2009 Zou et al.
2009/0229345 A1 9/2009 Van Kesteren
2010/0016717 A1* 1/2010 Dogra .................. A61B 5/0095 600/437
2010/0041987 A1* 2/2010 Manohar .............. A61B 5/0095 600/437
2011/0040176 A1* 2/2011 Razansky ................ A61B 5/05 600/425
2012/0125107 A1* 5/2012 Emelianov ......... A61B 5/02007 73/579
2012/0275262 A1 11/2012 Song et al.
2015/0265155 A1* 9/2015 Zalev .................. A61B 5/0095 600/407
2016/0143542 A1 5/2016 Bossy et al.
2017/0095227 A1* 4/2017 Park ....................... G10K 11/28
2017/0296063 A1* 10/2017 Osawa ................ A61B 5/0095

OTHER PUBLICATIONS

Wikipedia article “Diffraction” retrieved from https://en.wikipedia.org/wiki/Diffraction (Year: 2021).*
Wikipedia article for “Huygens-Fresnel principle” retrieved from https://en.wikipedia.org/wiki/Huygens%E2%80%93Fresnel_principle (Year: 2021).*
Nityananda, “Diffraction at a Straight Edge”, Resonance, May 2015 pp. 389-400. (Year: 2015).*
Balogun et al., Real-time full-field photoacoustic imaging using an ultrasonic camera, Journal of Biomedical Optics, vol. 15, No. 2, pp. 021318-1-021318-6 Mar. 2010.
Xia et al., Enhancement of photoacoustic tomography by ultrasonic computed tomography based on optical excitation of elements of a full-ring transducer array, Optics Letters, vol. 38, No. 16, pp. 3140-3143. Aug. 15, 2013.

* cited by examiner

DEVICES AND METHODS FOR PHOTOACOUSTIC TOMOGRAPHY

CROSS-REFERENCE TO RELATED APPLICATIONS

This application claims priority to U.S. Provisional Application No. 62/263,402, filed on Dec. 4, 2015, now, the disclosure of which is incorporated herein by reference.

STATEMENT REGARDING FEDERALLY SPONSORED RESEARCH

This invention was made with government support under Grant No. EY026411 awarded by the National Institutes of Health. The government has certain rights in the invention.

FIELD OF THE DISCLOSURE

The present disclosure relates to devices and methods for photoacoustic tomography.

BACKGROUND OF THE DISCLOSURE

Photoacoustic tomography (PAT) is playing an increasingly important role in biomedical imaging. The hybrid nature of PAT allows acquisition of high-resolution images beyond the optical diffusion limit, including deep-tissue imaging. Among various transducer arrays used in PAT, linear transducer arrays are commonly seen due to their low cost, hand-held convenience and easy adaption to clinical applications. A linear transducer array can be used in photoacoustic tomography because it is commercially available and readily allows ultrasound imaging.

However, the three-dimensional (3D) imaging capability of a linear array is limited, because its elevation resolution is much worse than its axial and lateral spatial resolutions. In a conventional linear-array PAT device, due to elevation focus from the acoustic lens, photoacoustic waves coming out of the focal zone cannot be received by the transducer. The loss in elevation receiving aperture limits the corresponding spatial resolution.

For instance, a particular array may have 0.144 mm axial and 0.298 mm lateral resolutions, but only a 1.5 mm elevation resolution (at the acoustic focus). Over the past few years, multiple methods have been proposed to address this issue. Some solutions combine linear and rotational scanning to achieve nearly isotropic 3D spatial resolution. Others propose a bi-directional scanning method with two array positions perpendicular to each other. In principle, these methods improve elevation resolution by converting the elevation direction into axial or lateral directions. However, such complicated scanning geometry often requires prolonged scanning times.

BRIEF SUMMARY OF THE DISCLOSURE

One embodiment of the present disclosure may be a photoacoustic tomography device comprising a laser positioned to produce acoustic waves in a sample, a transducer having a receiving aperture, a slit formed by one or more blades positioned substantially parallel to the receiving aperture of the transducer, an acoustic absorber affixed to each of the one or more blades along a surface proximal to the transducer, and a processor in electronic communication with the laser and the transducer configured to acquire data and reconstruct photoacoustic tomographic images based on the acquired data. The one or more blades may comprise a material having at least two times greater than or less than the acoustic impedance of water. The laser may be a pulsed laser.

In another embodiment, the device may further comprise a container, a medium dispersed within the container, and a sample support. The sample support and the one or more blades may be positioned within the medium. The sample support may be adjustable such that the sample can be positioned within a field of view of the transducer. The container may have an orifice covered with a material impermeable to the medium. The material may be configured to allow acoustic transmission to the transducer. The transducer can be immersed in the same medium as the blades or be separate from the medium by an impermeable material that is acoustically transparent. The field of view may be from one acoustic focal length to up to four acoustic focal lengths away from the receiving aperture.

In one embodiment, the transducer is a linear array transducer. The transducer may be adjustable and the one or more blades may be affixed to the transducer.

In another embodiment, the slit is formed by a first blade and a second blade, each positioned substantially parallel to the receiving aperture of the transducer. As such, the slit is formed between the first blade and second blade. The first blade and the second blade may be substantially parallel to each other in all planes. The slit may be positioned at an acoustic focus of the transducer. In one embodiment, the first blade has a proximal end in relation to an end of the second blade and the proximal end of the first blade and the end of the second blade are adjustable. The proximal end of the first blade and the end of the second blade may be independently adjustable. The proximal end of the first blade and the end of the second blade may be capable of forming or closing the slit. The width of the slit may be 0.5 to 1.0 times a central acoustic wavelength of the transducer.

In one embodiment, the device may further comprise a translation stage attached to the first blade or the second blade and a motion controller in electronic communication with the translation stage.

In one embodiment, the device may further comprise one or more fiber bundles for routing the output of the laser. In another embodiment, the device further comprises an array holder on which the blades and transducer are mounted.

Another embodiment of the present disclosure can be described as a method for performing photoacoustic tomography imaging. One embodiment comprises providing a sample, applying a laser to the sample such that sample produces acoustic waves, diffracting the acoustic waves using a slit formed by one or more blades positioned substantially parallel to the receiving aperture, receiving acoustic data at the transducer, storing the acoustic data in an electronic memory in electronic communication with the transducer, and generating an image based on the stored acoustic data.

In one embodiment, the method further comprises the steps of moving the sample or the transducer and slit to a next sampling position with a step distance less that the slit width and repeating the steps of applying, diffracting, receiving, storing, and moving until the overall moving distance covers a region of interest in the sample.

In one embodiment, the step of receiving acoustic data is triggered by the application of the laser to the sample.

In another embodiment, the slit is formed between a first blade substantially parallel to a receiving aperture of the transducer and a second blade substantially parallel to a receiving aperture of the transducer. At least one of the first blade or second blade may be adjustable. The method may further comprise the steps of adjusting the first blade or second blade to close the slit and generating a reference reading with the closed slit.

In one embodiment, the step of generating an image comprises a processor receiving the stored acoustic data, setting reconstruction parameters, defining a reconstruction area, reconstruction position, and pixel size, calculating an acoustic travelling path for the sample to each transducer element, and saving each calculated acoustic travelling path into a three-dimensional array. The reconstruction parameters may comprise slit position, speed of sound, and wavelength.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE DISCLOSURE

Figure 6:
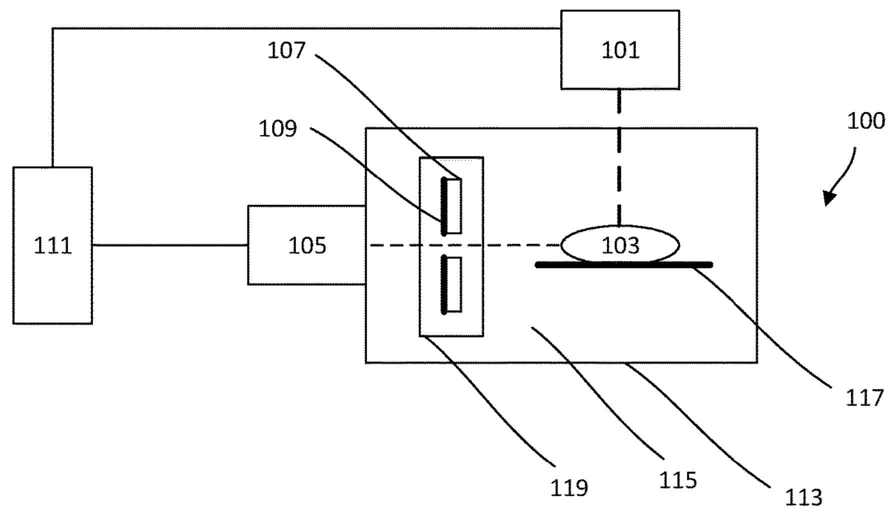
FIG. 6 is a block diagram of a photoacoustic tomography imaging device according to the present disclosure.
Figure 7:
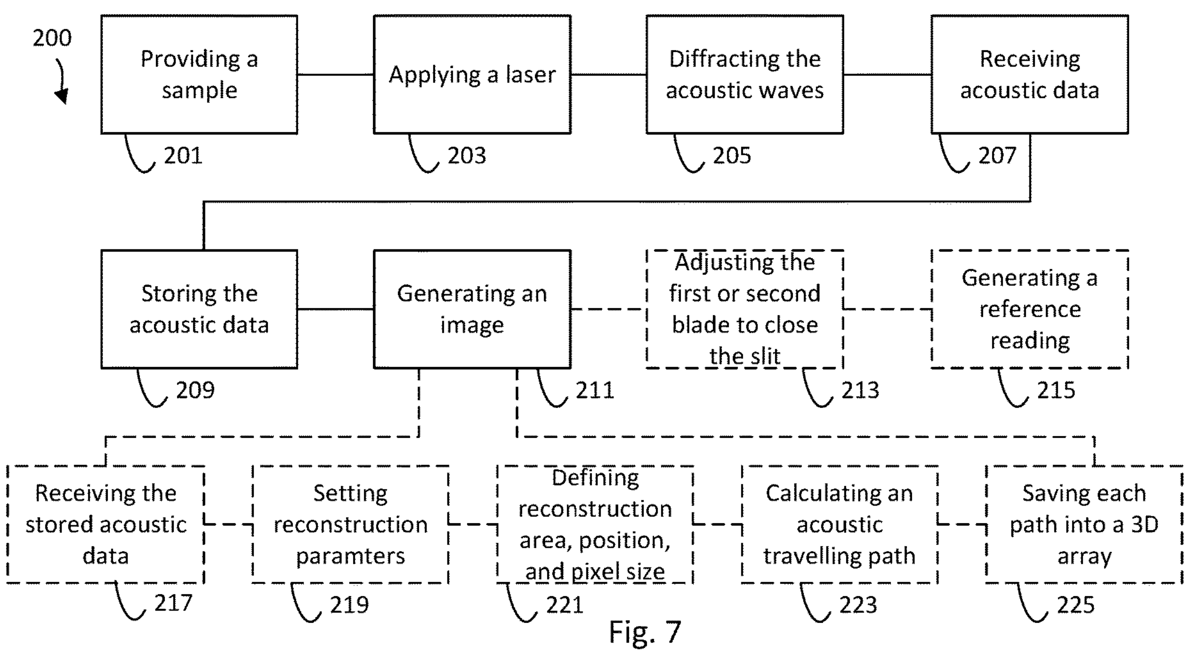
FIG. 7 is a flowchart of a photoacoustic tomography imaging method according to the present disclosure.

One embodiment of the present disclosure is a photoacoustic tomography device 100 as illustrated in FIG. 6. The device 100 comprises a laser 101 positioned to produce acoustic waves in a sample 103. The laser 101 may be a pulsed laser that emits light not in a continuous mode, but rather in the form of optical pulses. Depending on pulse duration, pulse energy, pulse repetition rate, and wavelength required, different methods for pulse generation and different types of pulsed lasers 101 may be used. The laser 101 may be aimed directly at the sample 103. In other embodiments, the laser 101 may be aimed at a series of lenses and mirrors which cause the energy emitted from the laser 101 to reach the sample 103. The sample 103 may be any organic or inorganic object that a user wishes to image. Typically the sample 103 is an organic object, such as tissue.

The device 100 further comprises a transducer 105 having a receiving aperture. The transducer 105 may be an electromagnetic acoustic transducer or a piezoelectric transducer.

The receiving aperture may be an area on the transducer 105 that receives acoustic waves. For a single element transducer, the aperture size may be the transducer element size. For an array transducer, the aperture may be all the elements that work together simultaneously. The transducer 105 may be a linear array transducer.

The device 100 further comprises a slit formed by one or more blades 107 positioned substantially parallel to the receiving aperture of the transducer 105. In the case of a single blade, the blade 107 may be a disc having an aperture to allow the transmission of acoustic energy. The slit may be at an acoustic focus of the transducer 105. The slit may be 0.5 to 1.0 times a central acoustic wavelength of the transducer 105. In one embodiment, the transducer 105 is adjustable and the one or more blades 107 are affixed to the transducer 105.

The device 100 further comprises an acoustic absorber 109 affixed to each of the one or more blades 107 along a surface proximal to the transducer 105. Acoustic absorption refers to the process by which a material, structure, or object takes in sound energy when sound waves are encountered, as opposed to reflecting the energy. Part of the absorbed energy is transformed into heat and part is transmitted through the absorbing body.

The device 100 further comprises a processor 111 in electronic communication with the laser 101 and the transducer 105 configured to acquire data and reconstruct photoacoustic tomographic images based on the acquired data. The processor 111 may be part of a single computer or multiple computers. For example, the processor 111 may be a cloud-based processor that operates utilizing the resources of one or more remotely located computers.

The device 100 may further comprise a container 113, a medium 115 dispersed within the container, and a sample support 117. The sample support 117 and the one or more blades 107 may be positioned within the medium. The sample support 117 may be adjustable such that the sample 103 can be positioned within a field of view of the transducer 105. The container may have an orifice (not shown in FIG. 6) covered with a material impermeable to the medium. However, the material may be configured to allow acoustic transmission to the transducer.

In some embodiments, the slit is formed by a first blade and a second blade positioned substantially parallel to the receiving aperture of the transducer 105, such that the slit is formed between the first blade and second blade. The first blade and the second blade may be substantially parallel to each other in all planes. The first blade and the second blade may be adjustable in one, two, or three dimensions. In some embodiments, one blade is fixed, while the other is adjustable. The one or more blades 107 may comprise a material having at least two times greater than or less than the acoustic impedance of water.

In one embodiment, the device 100 further comprises a translation stage 119 attached to the first blade or the second blade and a motion controller in electronic communication with the translation stage. The motion controller is not shown in FIG. 6.

Other embodiments of the present disclosure can be described as a method 200 for performing photoacoustic tomography imaging.

The method 200 comprises providing 201 a sample to be imaged and applying 203 a laser to the sample such that sample produces acoustic waves. The laser may be applied 203 intermittently or with varying degrees of power, frequency, or other parameters. The method further comprises diffracting 205 the acoustic waves using a slit formed by one or more blades positioned substantially parallel to the receiving aperture. The method 200 further comprises receiving 207 acoustic data at the transducer. In some embodiments, the step of receiving 207 acoustic data is triggered by the application of the laser to the sample.

In some embodiments, the transducer may be moved in order to receive 207 the acoustic data. In other embodiments, the transducer is fixed, but the slit changes. For example, when the slit is formed between a first blade substantially parallel to a receiving aperture of the transducer and a second blade substantially parallel to a receiving aperture of the transducer and at least one of the first blade or second blade is adjustable, the method 200 may further comprise adjusting 213 the first blade or second blade to close the slit and generating 215 a reference reading.

The method 200 further comprises storing 209 the acoustic data in an electronic memory in electronic communication with the transducer and generating 211 an image based on the stored acoustic data. Generating 211 an image may comprise the sub-step of receiving 217, at a processor, the stored acoustic data. Reconstruction parameters may be set 219, for example, automatically by the processor or through user interaction. A reconstruction area, reconstruction position, and pixel size may be defined 221. An acoustic travelling path may be calculated 223 based on the reconstruction parameters, reconstruction area, reconstruction position, and pixel size. The reconstruction parameters may comprise slit position, speed of sound, and wavelength. The calculated 223 acoustic travelling paths are saved 25 into a 3D array. The image is then formed based on the saved acoustic travelling paths.

One embodiment of the present disclosure can be described as a method for performing photoacoustic tomography. The method comprises diffracting acoustic waves from a sample using a slit between a first blade substantially parallel to a receiving aperture of a transducer and a second blade substantially parallel to the receiving aperture.

Another embodiment of the present disclosure can be described as a method for performing photoacoustic tomography. This method comprises placing a sample on a sample support; firing a laser at the sample to produce acoustic waves from the sample and trigger scanning and data acquisition programs; scanning the sample; diffracting the acoustic waves using a slit between a first blade substantially parallel to a receiving aperture of a transducer and a second blade substantially parallel to the receiving aperture; acquiring and saving data to a data acquisition device; and reconstructing the data using a data reconstruction device to generate an image.

Another embodiment of the present disclosure can be described as a photoacoustic tomography device. The device comprises a sample support, wherein the sample support is a distance from a plurality of blades. The plurality of blades comprises a first blade substantially parallel to a receiving aperture of the transducer and a second blade substantially parallel to the receiving aperture, wherein the plurality of blades is a distance from a transducer. The device also comprises a laser at a distance from the sample support sufficient to produce acoustic waves from a sample supported by the sample support. The device further comprises a data acquisition device electronically connected to the laser and transducer and a data reconstruction device electronically connected to the data acquisition device.

Another embodiment of the present disclosure can be described as a method for performing photoacoustic tomography. The method comprises placing a sample on a sample support, wherein the sample support is a distance from a plurality of blades. The plurality of blades comprise a first blade substantially parallel to a receiving aperture of the transducer and a second blade substantially parallel to the receiving aperture and the plurality of blades is a distance from a transducer. The method further comprises firing a laser at a distance from the sample support sufficient to produce acoustic waves from the sample and trigger scanning and data acquisition programs. The method further comprises scanning the sample and diffracting the acoustic waves using a slit between a first blade substantially parallel to a receiving aperture of a transducer and a second blade substantially parallel to the receiving aperture. The method further comprises acquiring and saving data to a data acquisition device electronically connected to the laser and transducer and reconstructing the data using a data reconstruction device electronically connected to the data acquisition device.

Another embodiment of the present disclosure may be described as a photoacoustic tomography device. The device may comprise a container and a medium dispersed in the container. The device may further comprise a sample support in contact with the medium, wherein the sample support is a distance from a plurality of blades. The plurality of blades is in contact with the medium and comprises a first blade substantially parallel to a receiving aperture of a transducer and a second blade substantially parallel to the receiving aperture. The plurality of blades is a distance from a transducer. The device further comprises a laser at a distance from the sample support sufficient to produce acoustic waves from a sample supported by the sample support. The device further comprises a data acquisition device electronically connected to the laser and transducer and a data reconstruction device electronically connected to the data acquisition device.

The ordering of method steps is not intended to limit the order of performance. Different orders of the steps are intended to be within the scope of the present disclosure.

As used herein, the transducer may comprise a single transducer or a linear array of transducers. Thus, all references to "transducer" refer to the transducing device in its entirety; i.e., when a linear array of transducers is used, the entire array is considered a "transducer." Some exemplary linear arrays are linear sequential transducer arrays (e.g. switched arrays) and linear phased transducer arrays (e.g., vector arrays or sector arrays).

As used herein, "adjustable" means moveable. In another embodiment, the sample support is adjustable. In another embodiment, the sample support is fixed but the transducer and slit position is adjustable. In a further embodiment, either the sample support or the transducer and slit combination is adjustable such that the sample can be placed within a field of view of the transducer.

As used herein, "sample" refers to any fractional or intact material or subject that is to be imaged, including intact organisms such as mammals and humans.

As used herein, words indicating direction such as "axial, lateral and elevation" and "x, y and z" are used only to indicate the relative positions of the components and are not intended as limitations on the orientation of the device.

In one embodiment, "substantially parallel" includes a deviation from parallelism of +/−5 degrees in any plane. In another embodiment, the blades may be substantially parallel to each other in all planes.

In one embodiment, an end of the first blade proximal to an end of the second blade are each i) fixed within the focal region of the transducer or ii) adjustable so that the ends can be positioned within the focal region of the transducer. In another embodiment, the ends are each i) fixed within the acoustic focus of the transducer or ii) adjustable so that the ends can be positioned within the acoustic focus of the transducer. Either or both of the ends may be adjustable. When both of the ends are adjustable, they may be adjustable independently or in concert with each other. When at least one blade is adjustable, the blade is adjustable so that the ends are i) capable of forming a slit between the ends and ii) capable of contacting each other to substantially close the slit such that the transducer aperture is substantially covered. In one embodiment, the blade is adjustable so that the ends are i) capable of forming a slit of ½ to 1 central acoustic wavelength of the transducer. When both blades are adjustable, the blades are adjustable in at least the plane parallel to the receiving aperture of the transducer. In one embodiment, the blades are adjustable solely in the plane parallel to the receiving aperture.

In one embodiment of the method where at least one blade is adjustable, the first blade and the second blade are brought into contact with each other to generate a reference reading. In an embodiment where a translation stage is used to adjust the adjustable blade, the reference reading is marked on the translation stage, and used to adjust the adjustable blade is adjusted to create a slit of ½ to 2 central acoustic wavelength of the transducer between the ends of the blades proximal to each other.

In another embodiment of the method where at least one blade is adjustable, at least one adjustable blade is adjusted to create a slit between the ends of the blades proximal to each other. In an embodiment, the slit is ½ to 2 central acoustic wavelength of the transducer. Either or both blades may be adjusted to form the slit.

The slit may be resized depending on the signal intensity. If the intensity is too weak, the slit may be enlarged. If the intensity is strong enough, a small slit may be used. The slit width determines the elevation spatial resolution. Intensity is affected by the absorption property of the sample.

The first blade and second blade may each comprise a material having at least two time greater than or less than the impedance of water, such as a metal or a metal alloy. The materials for each blade may be the same or different.

In one embodiment, the first blade and the second blade have a thickness of between ¼ acoustic wavelength and ½ acoustic wavelength in the blades' material(s). The blade may be covered by an acoustic absorbing material such as a foam, to minimize acoustic transmission through the blade.

In another embodiment, the first blade and the second blade each have a thickness which is a multiple of ¼ or ¾ of the acoustic wavelength in the blades' material(s), with the proviso that the thickness is not a multiple of ½ of the acoustic wavelength in the blades' material(s). These thicknesses may provide minimal acoustic transmission through the blade. The thickness of each blade may be the same or different.

The blades may be of a size sufficient to cover the transducer aperture when the blades are in contact with each other.

In one embodiment, the first blade and the second blade each have a length of between about 25 mm and about 56 mm. The blade length may be equal or greater than the length of the receiving aperture. The lengths of each blade may be the same or different.

In another embodiment, the first blade and the second blade each have a width of between about 5 mm and about 7.5 mm. Each blade's width may equal or be greater than half the width of the receiving aperture. The widths of each blade may be the same or different.

In another embodiment, an acoustic absorber is affixed to each of the first blade and the second blade along a blade edge proximal to the transducer. In one embodiment, the blade edge and the acoustic absorber affixed thereto are separated by a distance of between about 300 μm and about 1 mm. In an embodiment, the distance is about 300 μm. In one embodiment, the acoustic absorber is foam, such as High-Density Charcoal Open-Cell Foam (packaging foam). The acoustic absorber and the distance may be the same or different for each blade.

When both blades are fixed, the end of the first blade proximal to the end of the second blade may be separated from the end of the second blade by between ½ of the central acoustic wavelength of the transducer and 2 central acoustic wavelength of the transducer.

When either or both blades are adjustable, the end of the first blade proximal to the end of the second blade may be capable of being separated from the end of the second blade by between ½ of the central acoustic wavelength of the transducer and 2 central acoustic wavelength of the transducer.

When at least one blade is adjustable, the device may further comprise a translation stage attached to the adjustable blade. The device may further comprise a motion controller electronically connected to the translation stage. Exemplary motion controllers include the MT1-Z8 commercially available from Thorlabs.

In one embodiment, the transducer may be attached to the container. In another embodiment, the transducer may be adjacent to the container.

In another embodiment, the transducer array has a length of between about 25 mm and about 56 mm. In yet another embodiment, the transducer array has a width of between about 10 mm and about 15 mm. In still another embodiment, the transducer is an L7-4 transducer available from Philips, which has a central frequency of 5 MHz.

In one embodiment, the distance between the transducer and the plurality of blades is between ½ and 1½ acoustic focal distance of the transducer. In another embodiment, the distance between the transducer and the plurality of blades is the acoustic focal distance of the transducer.

In another embodiment, the distance between the transducer and the sample support may be less than or equal to three acoustic focal distances of the transducer. In another embodiment, the distance between the transducer and the sample support is less than or equal to 20 cm. In another embodiment, the transducer has an acoustic focal distance of 25 mm.

In one embodiment, the laser has a wavelength in the visible to near infrared range. In another embodiment, the laser has a wavelength of 532 nm. In another embodiment, the laser has a pulse width of less than or equal to 10 ns. In one embodiment, the pulse width is 10 ns. In yet another embodiment, the laser has a pulse repetition frequency of 10 Hz. In a further embodiment, the laser comprises a neodymium-doped yttrium aluminum garnet ("Nd:YAG") laser.

Attachment of the plurality of blades to the transducer may be useful for using the method in vivo where the sample remains stationary while the transducer moves to acquire the data. Thus, in one embodiment, the transducer is adjustable and the plurality of blades is affixed to the transducer. In another embodiment, the plurality of blades is affixed to the transducer by at least one arm. In another embodiment, each blade is attached to the transducer by a separate arm. In one embodiment of the method, the sample is moved to acquire the data while the transducer is stationary.

In addition, embodiments of the present disclosure may provide a transducer and a plurality of blades, wherein the plurality of blades comprise a first blade substantially parallel to a second blade, wherein the plurality of blades is affixed to the transducer at a distance from the transducer and substantially parallel to a receiving aperture of the transducer. In one embodiment, the plurality of blades is affixed to the transducer by at least one arm. In another embodiment, each blade is attached to the transducer by a separate arm.

The container may further comprise an orifice covered with a material impermeable to the medium, which material does not obstruct transmission to the transducer. The material may be a plastic such as polyvinyl chloride. In one embodiment, the material is a film. In another embodiment, the film has a thickness of less than or equal to 20 um. In another embodiment, the medium may be water. In yet another embodiment, the medium may be ultrasound gel.

Firing of the laser may trigger scanning and data acquisition programs. The transducer may convert acoustic signals into electric signals, which can be digitized by a data acquisition device such as DAQ. The DAQ device may save data into Matlab file type.

In one embodiment of the device and method, the data reconstruction device comprises a data reconstruction method as set forth below. The data reconstruction methods can be implemented, for example, using MATLAB.

Embodiments of the present disclosure may additionally provide a method of reconstructing data for photoacoustic tomography. The method may comprise loading all acquired data and imaging parameters into a computing program. The method may further comprise using the computing program, setting reconstruction parameters, comprising slit position, speed of sound, and wavelength. The method may further comprise, using the computing program, defining a reconstruction area, reconstruction position, and pixel size. The method may further comprise, using the computing program, creating a three-dimensional array to save data. The method may further comprise, using the computing program, converting a CPU array into a GPU array. The method may further comprise, using the computing program, processing data by a GPU to accelerate reconstruction speed. The method may further comprise using the computing program, calculating the acoustic travelling path for the sample to each transducer element. The method may further comprise, using the computing program, saving the acoustic travelling path calculations in a three dimensional array. The method may further comprise, using the computing program, converting bipolar data into unipolar data to make all signals positive.

The speed of sound in medium is almost a constant and only slightly changes with temperature. The speed can be adjusted to sharpen the image.

In one embodiment of the method, the computing program converts the three-dimensional array in a graphics processing unit ("GPU") array prior to calculating the acoustic traveling path.

In one exemplary embodiment, the data reconstruction device uses the following computer code:

```
        (1) Load all experimental data and imaging parameters into MATLAB
    % 3D RECONSTRUCTION CODE FOR L4-7 TRANSDUCER
    % True 3D reconstruction with GPU
    % JUN XIA, JAN 20, 2015
    clear all;
    clc
    load L7_4FlashExtTrig_dualdisplay_64_noProcess; % load the daq parameters
    load 300PA; % load the raw data
        (2) Set reconstruction parameters, such as slit position, speed of sound, and
wavelength.
    rfdata = d(1:2000,:,:);
    fs = Trans.frequency*4; % 30 MHz
    b = subfunc_exact_simp(rfdata,fs); % use a ramp filter to do differentiation
    rfdata = b(:,:,1:1:end); clear b;
    interval=0.1; % distance between scan lines in elevation
    SFormat. endDepth = size(rfdata,1);
    IntFac =1;
    dArrayPlate = 25.07; % distance between array and metal plate
    Len_R = dArrayPlate; % the array focal length
    rfdataH = zeros(size(rfdata,1)*IntFac,size(rfdata,2),size(rfdata,3));
    for ii = 1:size(rfdata,3)
        for kk = 1:size(rfdata,2)
            rfdataH(:,kk,ii) = interp(rfdata(:,kk,ii), IntFac);
        end
    rfdata = rfdataH;
    fs = Trans.frequency*4*IntFac; % 30 MHz
    Hlines = size(rfdata,3); % number of elevation scan lines
    sos = 1.51;
    cAngle =80*pi/180; % critical receiving angle in 2D plane (40 degrees)
    wavelength = sos/Trans.frequency;
        (3) Define the reconstruction area, reconstruction position and pixel size.
    zDepthOffset =58; % in mm
    xDepthOffset =0;
    yDepthOffset =0;
    lines = Trans.numelements;
    ResFactor =10; %defines the resolution: how many pixels in 1 mm along axial and lateral
    directions
```

-continued

```
YResFactor =10; %defines the resolution: how many pixels in 1 mm along elevation
direction
pixel_size = 1/ResFactor; % mm, the lateral and axial directs will have the same pixel
size
Ypixel_size = 1/YResFactor; % mm, the pixel size in elevation
%%%%%%%%%%%%%%%%%%%%%%%%%%%%%%%%%%%%%%%%%%%%
z_size = 20; Nz = floor(z_size*ResFactor); %defines the total reconstruction area in mm
x_size = 35; Nx = floor(x_size*ResFactor);
y_size = 25; Ny = floor(y_size*YResFactor);
x_img0 =round(xDepthOffset)+(0:(Nx−1))*pixel_size-pixel_size*(Nx−1)/2; % define
reconstruction locations along lateral direction (mm)
z_img0 =round(zDepthOffset) + (0:(Nz−1))*pixel_size ; % along axial direction
y_img0 =round(yDepthOffset)+(0:(Ny−1))*Ypixel_size-Ypixel_size*(Ny−1)/2; % along
elevation
% use element location to create a 2D matrix, unit in mm
x0 =(0:(Trans.numelements−1))*Trans.spacingMm−
Trans.spacingMm*(Trans.numelements−1)/2;
```

(4) Create a three dimensions array in MATLAB to save data.

```
% conversion into 2D or 3D
temp = ones (Nz,1);
x_img=temp*x_img0;
temp = ones(1,Nx);
z_img =z_img0'*temp;
y3D = zeros(Nz,Nx,Ny);
for iH = 1:Ny
    y3D(:,:,iH)=ones(Nz,Nx)*y_img0(iH);
end
eleWidthWl = Trans.elementWidth / wavelength;
TransSen = zeros(Nz,Nx,lines);
angleall = zeros(Nz,Nx,lines);
y = (1:Hlines)−(Hlines+1)/2;
y0 = y*interval; % transducer positions in elevation
pa_img = zeros(Nz,Nx,Ny);
rfdata(1,:,:)=0;
```

(5) Convert CPU array into GPU array then process data by GPU to accelerate reconstruction speed.

```
% % convert CPU array into GPU array
x_img = gpuArray(x_img);x0 = gpuArray(x0);z_img = gpuArray(z_img);
y3D = gpuArray(y3D); y0 = gpuArray(y0);pa_img = gpuArray(pa_img);
h = waitbar(0,'Please wait...'); % create a waitbar
```

(6) Calculate the acoustic traveling path for the object to each transducer element and save them into a three dimensional array.

```
for iH = 1:Hlines
    tic % calculate running time
    rfdataI = gpuArray(rfdata(:,:,iH));
    % rfdataI = rfdata(:,:,iH);
    for iLine = 1:lines
         r = sqrt((x_img − x0(iLine)).^2 +
              z_img.^2);%+Trans.lensCorrection./cos(atan(abs((x_img −
              x0(iLine)))./z_img));
        r = repmat(r,[1,1,Ny]);
        Angle_line = atan(abs(x_img−x0(iLine))./z_img);
        Angle_line = repmat(Angle_line,[1,1,Ny]);
        din = (r-Len_R./cos(Angle_line));
        r3D = sqrt(din.^2+(y3D−y0(iH)).^2).*sign(din)+Len_R./cos(Angle_line);
        Angle_line2 =1; %(atan(abs((y3D−y0(iH))./din))<
              atan(abs(7.0./(Len_R./cos(Angle_line))))); % 7 mm is the half
              height of array element
        Angle_line(Angle_line==0)=0.001;
        TransSen =
              abs(cos((Angle_line)).*(sin(eleWidthWl*pi*sin((Angle_line)))./
              (eleWidthWl*pi*sin((Angle_line)))));
        idx= round((r3D/sos)*fs)−Receive(1).startDepth*4+3*IntFac;
        inrange = (idx >= 1) & (idx <
              SFormat.endDepth)&(Angle_line<=cAngle);
        idx = (inrange).*idx + (1−inrange).*1; % if in the range, index = idx.
              otherwise index = zsamples (value = 0)
        % aa = find(isnan(idx));idx(aa)=1;
        itemp_Rf = rfdataI(:,iLine);
        pa_img = itemp_Rf(idx).*TransSen.*Angle_line2+pa_img;
    end
    timen = toc;
    timen = (Hlines-iH)*timen/60;
    waitbar(iH/Hlines,h,[sprintf('%12.1f',timen) ' mins remaining;']);
```

-continued

```
end
delete(h);
        (7) Convert bipolar data to unipolar to make all signal positive.
pa_img = gather(pa_img);
pa_imgH = pa_img;
for i=1:Ny
        pa_imgH(:,:,i)=abs(hilbert(pa_img(:,:,i)));
end
```

Slit-enabled three-dimensional photoacoustic tomography addresses the issue of long-scanning times. The metal slit, placed at the array focus, causes the incoming photoacoustic waves to diffract along the elevation direction and hence significantly improves the elevation detection aperture and resolution. One exemplary embodiment of the present disclosure was tested in both phantoms and animals. The slit improved the elevation resolution by ten times without compromising scanning time. Three-dimensional reconstruction calculates the optimum traveling path as determined by slit diffraction.

Slit-enabled PAT significantly improved the elevation resolution of the linear transducer array. Besides improvement in elevation resolution, the slit also improves the SNR due to a larger receiving aperture. Compared to existing approaches to improve elevation resolution, embodiments of the present disclosure has higher imaging speed and requires no change to the scanning geometry. Thus it can be easily adapted to any existing linear-array PAT devices. Due to limitations in laser pulse repetition rate (10 Hz), animals were only imaged in situ (as animal motion prevents 3D reconstruction). However, kHz high power pulsed lasers are commercially available and can be used for high speed in vivo imaging. Also, some embodiments may not achieve true isotropic resolution in 3D due to the large element pitch, which defines the lateral resolution. However, a linear phased array or a custom-designed array with smaller pitch can be used to address this issue.

Exemplary Embodiment

Figure 1:
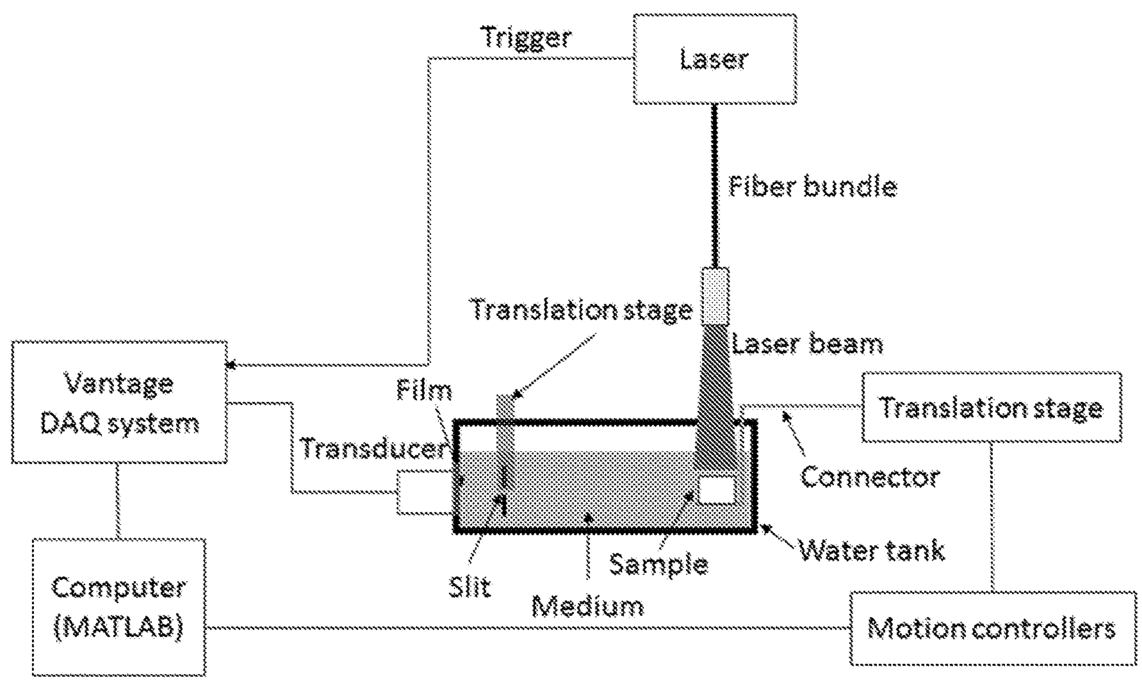
FIG. 1 is a block diagram of a slit-enabled linear array photoacoustic imaging device.

The following exemplary device and method is based on acoustic diffraction through a thin slit placed along the acoustic focus of the array (FIG. 1). The thin slit diffracts the incoming photoacoustic waves and hence improves the receiving aperture along elevation direction. As shown in FIG. 1, in a conventional linear-array PAT device (FIG. 1*a*), due to elevation focus from the acoustic lens, photoacoustic waves coming out of the field of view cannot be received by the transducer. The loss in elevation receiving aperture limits the corresponding spatial resolution. The metal slit (with a width close to the 300 μm central acoustic wavelength) eliminates the acoustic focus, allowing waves coming out of the field of view to still reach the transducer (FIG. 1*b*). The increased receiving aperture can greatly improve the elevation resolution. Compared to other approaches, this method does not require any modification on scanning geometry—only one elevation scan is needed as in conventional 3D PAT. This unique feature possesses significant advantage over existing approaches.

Experiment 1

Figure 2:
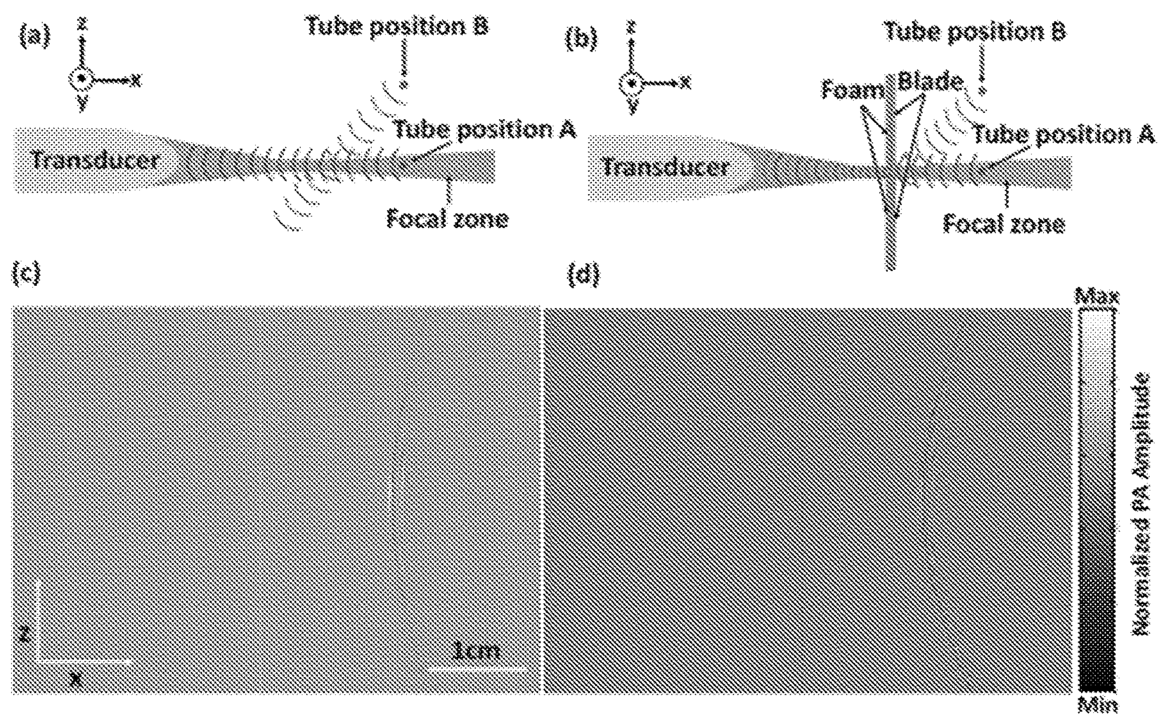
FIG. 2 depicts the principle of a slit-enabled photoacoustic tomography device.

A tube filled with black ink was imaged. The tube is placed along the lateral direction (y axis) of the array and can be scanned along the elevation direction (z axis) through a translation stage. In the z-x plane, the tube looks like a point source (FIGS. 2*a* and 2*b*). Acoustic signals are received by a 128-element linear transducer array (ATL/Philips L7-4) with 5 MHz central frequency and elevation focus at 25 mm. Light illumination was achieved by an Nd:YAG laser (Surelite SL III-10, Continuum) with <10 ns pulses width and 10 Hz pulse repetition frequency (PRF). The output wavelength is 532 nm and the energy of each pulse is 18 mJ. PA signals received by the L7-4 array were multiplexed and digitalized by a 64-channel ultrasound data acquisition device (Vantage, Verasonics Inc., Redmond, Wash.). The thin slit was formed by two metal blades (0.5 mm thickness). The bottom blade was fixed in position while the top blade was mounted on a translation stage, which allowed easy and precise control of the slit opening. While the blade thickness is not multiples of half acoustic wavelength in stainless steel (0.58 mm), a small portion of sound energy may still transmit directly through the plate. To prevent this, double-faced tape was used to attach a 5 mm High-Density Charcoal Open-Cell Foam (packaging foam) on the back surface of the blade (facing the transducer) as an acoustic absorber. As a demonstration of the principle, 40 mm with 0.1 mm step size was scanned over. The entire scan took 80 seconds (40 mm/0.1 mm/5 Hz).

FIG. 2*c* shows a segment of raw-channel data (in z-x plane) acquired without the use of the metal slit. Because of the limited receiving aperture along elevation direction (the gray-colored region represents the acoustic receiving zone), the transducer gradually misses tube signal while it is moved from position A to position B. Thus in FIG. 2*c*, only the central region shows strong tube signal. Once the metal slit has been added (FIG. 2*b*), incoming acoustic waves will diffract through the slit, which changes the wave propagation direction. The tube can now be detected within the entire 40-mm scanning range (FIG. 2*d*). In principle, the slit can be placed anywhere along the lateral direction. The acoustic focal position was chosen because it offers the highest detection sensitivity and minimum signal loss.

Figure 3:
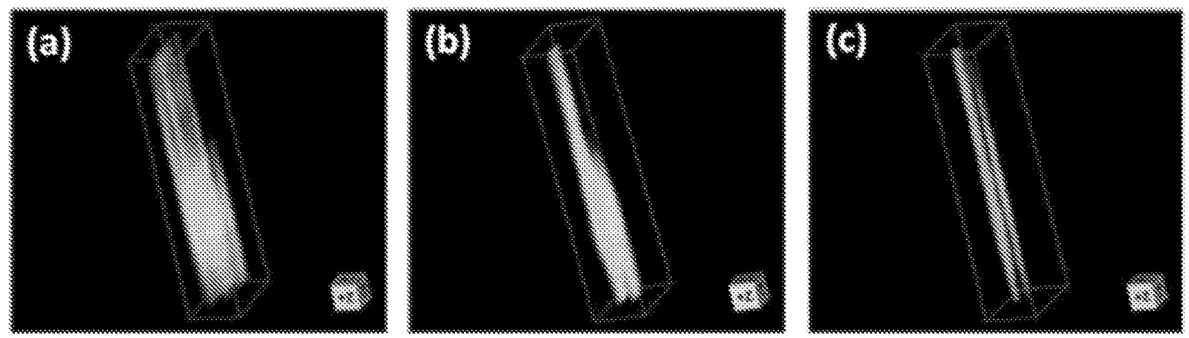
FIG. 3 shows reconstructed images of a single tube using three different reconstruction algorithms.

Reconstructed images of the single tube are shown in FIG. 3. For the conventional PAT, two reconstruction methods were used. The first method reconstructs each 2D image individually and then all images are stacked to form a 3D image. This is the most commonly used approach to form a 3D image from linear array. The second method reconstructs the same dataset in 3D using the focal-line concept, which improves the elevation resolution up to the size of the elevation focal height (~1.5 mm). Image reconstruction with slit is similar to the focal-line reconstruction approach. The delay time of each point source in 3D space is calculated based on the following two principles: (a) wave propagation in x-y plane is unaffected by the slit; and (b) wave propagation in z-x plane has two segments, first from point source to slit and then from slit to transducer element. For simplicity, the three different reconstruction/imaging methods are named as 2D-stack PAT, 3D-focal-line PAT, and slit-PAT. As shown in FIG. 3*a*, 2D-stack PAT has the poorest elevation resolution (along z-axis). The tube can barely be identified. While 3D-focal-line PAT provides better images of tube structure, the tube image is still blurred along elevation direction (FIG. 3*b*). As expected, slit-PAT offers the highest elevation resolution and the tube can be clearly identified (FIG. 3*c*). It should be noted that, in all these images, two tubes are seen instead of one due to the boundary built up effect along axial direction. The distance between the two "tubes" is quantified to be 0.5 mm, which is the inner diameter of the tube.

TABLE 1

Elevation resolution and SNR analysis of different imaging/reconstruction methods

| | 2D-stack PAT | 3D-focal-line PAT | Slit-PAT |
|---|---|---|---|
| Resolution | 3.52 mm | 1.67 mm | 0.33 mm |
| SNR | 16.2 | 136.7 | 62.7 |

Table 1 summarizes the elevation resolution and signal-to-noise ratio (SNR) of three imaging/reconstruction methods. The elevation resolution is defined as the full-width-at-half-maximum (FWHM) of the first boundary of the tube along the elevation direction. It can be seen that 2D-stack PAT provides the worst elevation resolution. With focal-line reconstruction, the resolution was improved by two time and the value is close to the height of the elevation focus (1.5 mm). Slit-PAT further improves resolution by almost five times to 0.33 mm, which is close to the 0.3 mm slit opening. In total, slit-PAT offers ten times better elevation resolution than 2D-stack PAT. 0.33 mm is close to the lateral resolution (0.298 mm) and is not far from the axial resolution (0.144 mm). Because the slit also blocks some incoming photoacoustic signals, SNR was analyzed. The signal intensity was calculated by averaging signals within a small region in the tube. Noise was estimated by calculating the standard deviation of signals in a background region. Main source of noise was the electronic noise in the PAT data acquisition device. As shown in Table 1, the slit-PAT SNR is actually four times better than that of 2D-stack PAT. This is due to the fact that, in slit-PAT, the transducer receives signal from all 400 scanning positions, whose data are coherently summed during reconstruction. This procedure reduces the noise by 20 times. In terms of signal intensity, the slit reduces the signal by 5 times (0.3 mm slit opening/1.5 mm elevation focal height). Thus the overall improvement in SNR is 4 times [$\frac{1}{5}$ signal/($\frac{1}{20}$ noise)]. As expected, 3D-focal-line PAT provides the highest SNR. However, due to the limited receiving aperture, its SNR is only two times better than that of slit-PAT, but with five times worse elevation resolution. The resolution and SNR results demonstrate that slit-PAT remarkably improves the elevation resolution without compromising the SNR.

Experiment 2

Figure 4:
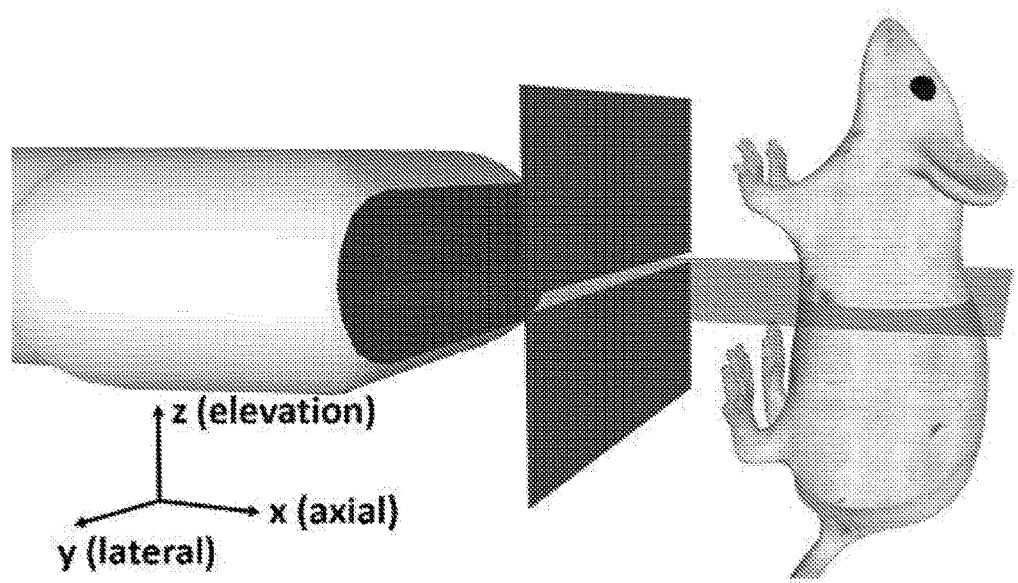
FIG. 4 is three-dimensional drawing of the in situ experiment setup.

To further demonstrate the imaging capability, a mouse abdomen was imaged in situ (FIG. 4). In addition to the hemoglobin contrast, ZnBNc nanonaps were also used as an intestine-confined contrast agent. To match the absorption peak of ZnBNc nanonaps (710 nm), light coming out of an optical parametric oscillator (OPO) laser pumped by the Nd:YAG laser was used. The experiment was performed on a 23 g female nude mouse been fasted overnight with access to only water. Before the experiment, the mouse was administered via gavage 0.2 mL of ZnBNc nanonaps with an absorbance of 500 at 710 nm. Thirty minutes after gavage, the mouse was sacrificed and mounted vertically on the device with the abdomen facing the transducer array (FIG. 3). In both the conventional and slit-enabled PAT, the mouse was scanned vertically over 25 mm, which covers the entire small intestine region. For better illustration, the reconstructed 3D image was maximum amplitude projected and depth-encoded along the axial direction of the array (posterior direction of the animal body).

Figure 5:
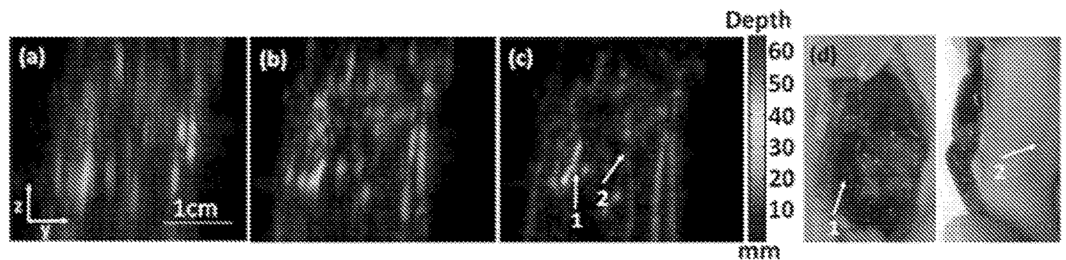
FIG. 5 depicts the results of an in situ experiment of mouse abdomen.

FIG. 5*a* shows the depth-encoded image of 2D-stack PAT. Anatomical features or structures were not recognizable, due to the poor elevation resolution. FIG. 5*b* shows depth-encoded image of 3D-focal-line PAT, where some skin vessels could be recognized. However, body structures were still difficult to recognize. FIG. 5*c* shows the depth-encoded image of slit-PAT. Here the intestine and several additional skin vessels can be clearly identified. In particular, a pair of crossed skin vessels (arrow 2) is only made visible with the high elevation resolution. These features agree well with photos of exposed animal acquired after the experiment (FIG. 5*d*).

Figure 8:
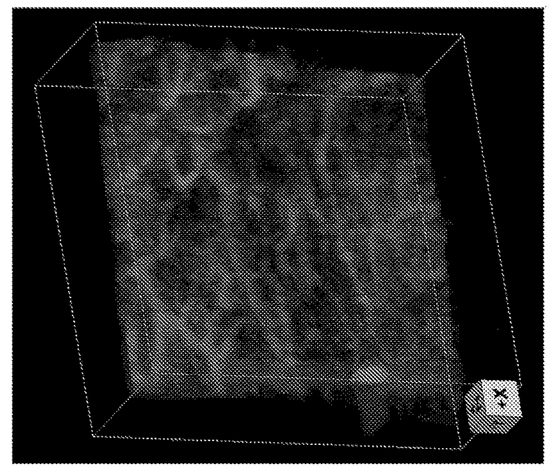
FIG. 8 is a photoacoustic tomography image volume captured using an embodiment of the present disclosure.

Another embodiment of the present disclosure uses a slit holder that can be directly mounted to the transducer array for easy adjustment of slit width and simultaneous scanning of both the array and the slit. To enlarge the imaging field of view, a bifurcated line fiber bundle may be used which moves simultaneously with the array and the slit. With some changes to the data acquisition device, imaging speed may be doubled. For example, one embodiment can image a 3.8×4 $cm^2$ region within 40 seconds and the object only needs to be coupled through ultrasound gel. This embodiment was capable of imaging vasculatures in the palm and forearm of human volunteers (see FIG. 8).

Unlike conventional optical imaging, the photoacoustic frequency spectrum is determined by the object and it typically contains a wide range of acoustic frequencies (wavelengths). Thus the slit width may be adjustable based on features of the object.

Figure 9A:
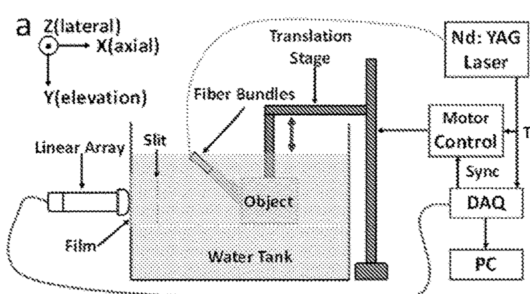
FIGS. 9A and 9B are schematic drawings of devices according to the present disclosure.
Figure 9B:
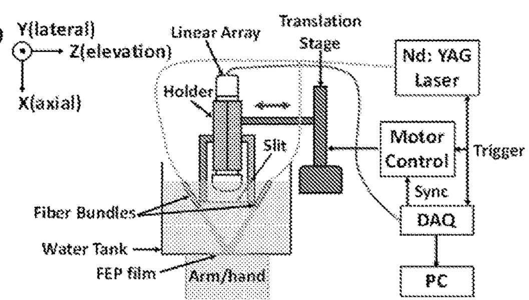

FIGS. 9A and 9B compare two designs of the present disclosure. In FIG. 9A, the transducer, slit and object were all immersed in water and the object was scanned in the vertical direction for 3D imaging. Imaging of objects in vivo could be challenging in this design. For the device in FIG. 9B, an open-bottom water tank is used, and only the transducer and slit are submerged in water. The scanning direction was also changed from vertical to horizontal, as identified by double arrows. The bottom of the water tank was sealed with 0.05 mm thickness FEP plastic film (85905K64, McMASTER-Carr) and the object could be imaged through this window. FEP plastic was chosen here due to its high strength and transparent color. In some embodiments, the slit may be formed by two 316 stainless steel blades. This type of steel has excellent corrosion resistance and is designed to be used in marine applications. The two steel sheets have a thickness of 0.3 mm which is a quarter of the acoustic wavelength in stainless steel (1.2 mm). This thickness minimizes the transmitted sound energy. An array holder was used to mount the two steel sheets in front of the transducer array. In the holder, both steel sheets are compressed by a set of screws. The slit width can be easily adjusted by loosening the screws. In order to quickly reach the desired slit width, several aluminum sheets were machined with thicknesses ranging from 0.3 mm to 2.4 mm with a step size of 0.3 mm. To adjust the slit width, the corresponding aluminum sheets are inserted and aligned to make a close fit and then tighten the locking screws.

Light illumination was provided by an Nd:YAG laser (Surelite SL III-10, Continuum) with <10 ns pulses width and 10 Hz pulse repetition frequency (PRF). 532 nm and 1064 nm output wavelengths were used for phantom and in vivo experiments, respectively. For light delivery, a bifurcated fiber bundle was used with a 1.1-cm-diameter circular input and two 5.1-cm-length line outputs. The beam on the object's surface was approximately 2.5 cm×6.0 cm in size. Compared to the single circular fiber bundle, the line fibers provide a more uniform illumination within the rectangular field of view. During the experiment, the fiber bundles were mounted on the slit holder and moved simultaneously with the transducer. While, in this design, the optical absorption map changes at each scanning step, which introduces inconsistency into the device equation. However, the design improves the light intensity around the region of focus and allows for imaging a larger object. The data acquisition (DAQ) unit used in this device has 128 channels (Vantage-128, Verasonics Inc.) and the acquisition speed is two times faster than the original device with a 64-channel DAQ unit. Acoustic signals are detected by a 128-element linear transducer array (ATL/Philips L7-4) with 5 MHz central frequency, 3.8 cm lateral length, and 2.5 cm elevation focus. For scanning a 3.8 cm×4 cm region at a 0.1 mm step size, the entire experiment took 40 seconds. The digitized photoacoustic signals were then reconstructed through a focal-line-based algorithm that treats the slit as a virtual line detector to calculate the acoustic time of arrival between each acoustic transducer and reconstruction point. The reconstructed image represents the product of optical absorption and fluence. For better visualization, the reconstructed 3D image was projected along the axial direction of transducer array to form a depth-encoded MIP (Max Intensity Projection) image.

Figure 10:
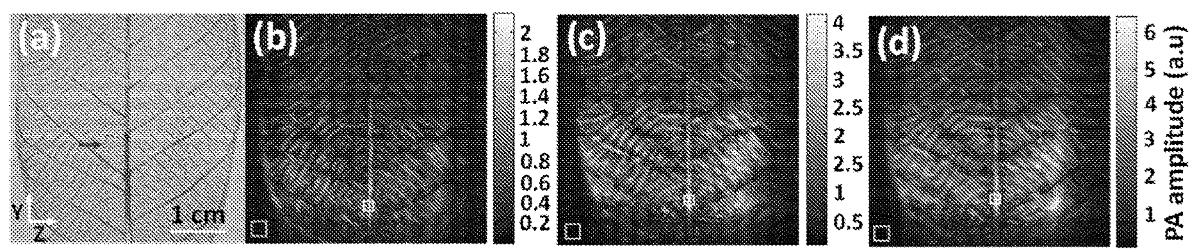
FIG. 10 illustrates a leaf phantom experiment performed at different slit widths using devices and methods of the present disclosure.

To test the effect of different slit widths, a leaf phantom was imaged. The phantom was placed at 4 cm away from the slit to ensure a large elevation coverage (the diffraction far field). The energy on the leaf phantom's surface was 15 mJ/cm$^2$. An area of 3.8 cm×4 cm was scanned along the elevation direction (z axis, FIG. 10*a*). FIG. 10 shows maximum intensity projected (MIP) images acquired at different slit widths. It can be seen that as the slit width increases, the image becomes blurry along the elevation (z) direction. For instance, in FIG. 10*b*, both the midrib, primary veins and secondary veins are distinctly resolved, and the features look very similar to the leaf photograph (FIG. 10*a*). FIG. 10*c* still resolves features of the midrib and primary veins because of their large diameter, but the secondary veins become blurry due to the decreased resolution. FIG. 10*d* provides the most blurry image due to its largest slit width. Only the midrib looks as sharp as other images. To quantify the elevation resolution, a small leaf vein was chosen growing along the elevation direction (arrow, FIG. 10*a*). The diameter of this vein is approximately 200 μm, which is less than the smallest slit width. For each slit width, the vein was identified in the 3D dataset and the resolution quantified by calculating full width at half maximum (FWHM) along the elevation resolution. The resolutions are very close to the corresponding slit width. This result can be explained by the Fraunhofer diffraction theory which states that the diffraction angle θ is proportional to the ratio of wavelength (λ) and slit width (d): $\sin(\theta) \approx \lambda/d$. As the slit width increases, the diffraction angle of high frequency ultrasound signal (small λ) decreases, which, in term, reduces the elevation coverage and the corresponding spatial resolution. In this regard, the slit works as a tool to effectively control the receiving angle and frequency components along the elevation direction.

While an increased slit width degrades the spatial resolution, it improves the detected signal amplitude, because a larger slit allows more signals to pass through. In FIGS. 10*b*-10*d*, the upper limit of the color bar corresponds to the maximum value in each image. It can be seen that changes in maximum intensity is close to the slit width ratio (1:2:3). The signal to noise (SNR) ratio was also quantified at different slit widths. The area used to calculate SNR were identified by boxes: the box shows the area for signal calculation (average) while the green box indicates the area for noise calculation (standard deviation, located in the lower left of the image). Similar to the resolution study, the calculation was performed on the original 3D dataset. As expected, as the slit width increases, the SNR also increases. These results indicate that, in order to reach an optimum balance between spatial resolution and SNR, the slit width should be chosen based on the object feature.

Figure 11:
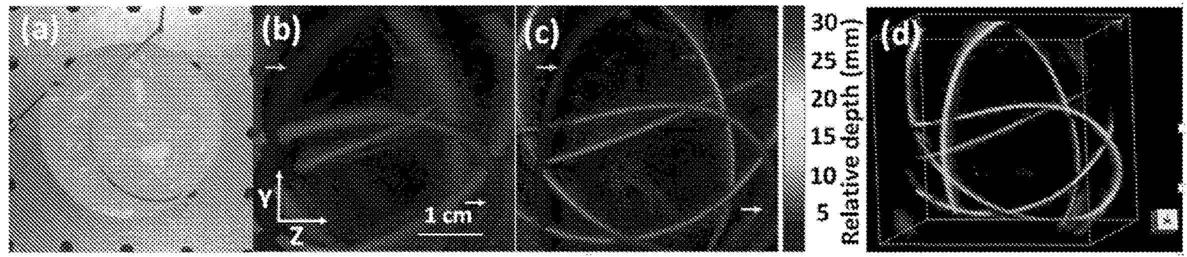
FIG. 11 illustrates a tube phantom experiment performed using devices and methods of the present disclosure.

To test the imaging capability for structures distributed in 3D, a tube filled with black ink was imaged. The tube was embedded in an agar gel (3% in weight) whose optical scattering property mimics that of breast tissue (FIG. 11*a*). Inside the gel, the tube was twisted to form a structure in 3D. Because the tube has an inner diameter of 0.5 mm, a slit width of 0.6 mm was chosen. To confirm the elevation resolution improvement, the same phantom was scanned by conventional PAT without slit. In that experiment, the phantom's top surface was located near the transducer focus (25 mm), where the transducer had the highest elevation resolution. FIG. 11*b* and FIG. 11*c* are depth-encoded images of tube phantom reconstructed by conventional PAT and slit PAT, respectively. It can be clearly seen that in FIG. 11*b* the tube looks blurry along the elevation direction (z) and the blurriness increases as the tube is further away from the elevation focus (increased relative depth). In contrast, the tube in FIGS. 11*c* and 11*d* looks very clear and the elevation diameter remains the same at different depths. The elevation resolution was also quantified at three tube cross sections, as identified by arrows (FIG. 11). The average resolution of slit PAT is 0.64 mm, which is close to the 0.60 mm slit width. For conventional PAT, the average resolution is 1.50 mm. Thus slit-PAT improves the elevation resolution by at least two times. These data also revealed that the slit technique works well over a large axial depth of over 25 mm.

Figure 12:
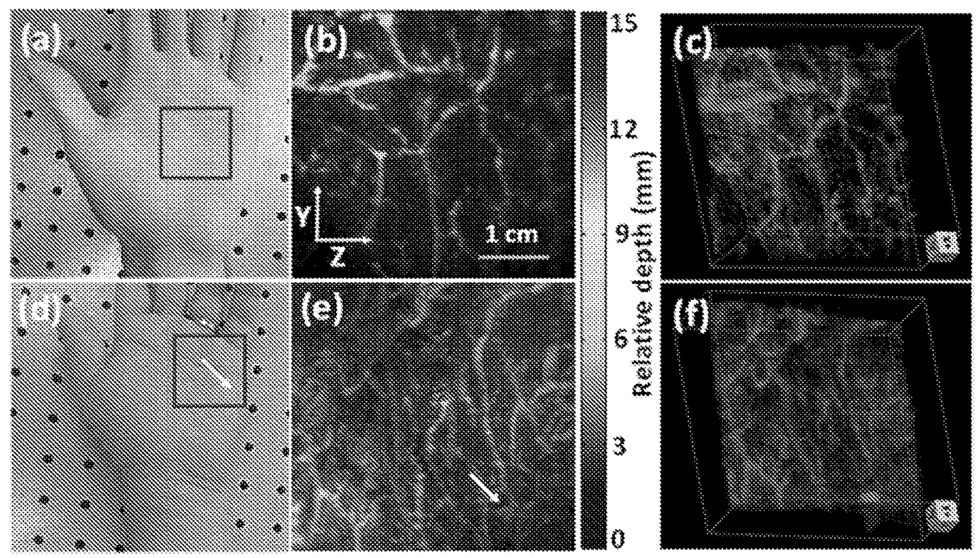
FIG. 12 illustrates a palm experiment performed using devices and methods of the present disclosure.

To demonstrate the in vivo imaging capability of the device, the palms of two volunteers were imaged. An area of 3.8 cm×4 cm was imaged as indicated by boxes in FIGS. 12*a* and 12*d*. For the second volunteer, there is a nevus located near the bottom right corner of the scanning area, as identified by an arrow. The energy on the skin surface was 27 mJ/cm$^2$, which is much lower than the ANSI safety limit of 100 mJ/cm$^2$. A slit width of 600 μm was set for imaging vessels with close to or larger than 600 μm diameter. The depth encoded results are shown in FIGS. 12*b* and 12*e*. Rich vascular structures can be clearly seen in both images. For the second volunteer, the nevus can also be identified in the photoacoustic image (arrow, FIG. 4*e*). The depth encoded color indicates that the disclosed techniques can clearly resolve features distributed over 15 mm in depth. Such a performance could not be acquired by conventional linear-array-based PAT. For better illustration, 3D volume images are shown in FIGS. 12*c* and 12*f*.

Figure 13:
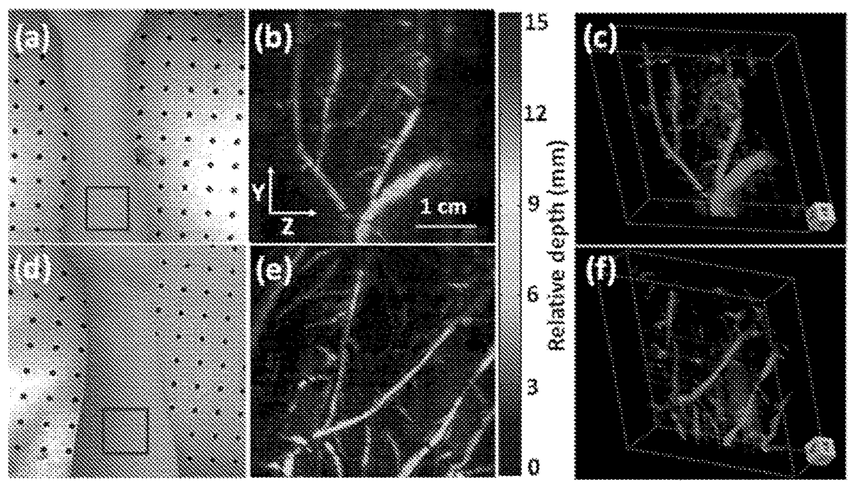
FIG. 13 illustrates a palm experiment performed using devices and methods of the present disclosure.

The forearms of two volunteers were imaged to validate that the device can image larger vessels. The scanning size and optical intensity were set to be the same as the previous hand experiment. The slit width was increased to 900 μm because the forearm vessels are larger than that of the palm. The boxes in FIGS. 13*a* and 13*d* indicate the imaged regions for volunteer 1 and 2, respectively. No blood vessels could be identified in photographs due to light scattering. In contrast, the PA images (FIGS. 13*b* and 13*e*) clearly show vessels at various depths. Compared to palm images where vessels are small and densely distributed, the arm vessels are much larger and more sparsely distributed. Because the imaged region of the arm was flatter than that of the palm, the relative depth of blood vessels in the arm ranged from 0~10 mm, while the palm vessels ranged from 0~15 mm depths. Again, for better illustration, 3D volumetric images were generated and are shown in FIGS. 13*c* and 13*f*.

In conclusion, the images show uniform spatial resolution over the entire reconstruction volume, demonstrating potential for clinical imaging of tumor angiogenesis or vascular disorders in the upper extremities. Compared to other techniques to improve elevation resolution in a linear array, the presently disclosed methods possess the highest imaging speed with the best spatial resolution. Future improvements can be made to increase the lateral field of view, to further improve the imaging speed, and to incorporate ultrasound imaging. The slit principle can also be applied in ultrasound to achieve dual-mode imaging. Implementing these improvements will allow us to build a high speed and high resolution vascular and structural imaging system for clinical use.

Although the present disclosure has been described with respect to one or more particular embodiments, it will be understood that other embodiments of the present disclosure may be made without departing from the spirit and scope of the present disclosure. Hence, the present disclosure is deemed limited only by the appended claims and the reasonable interpretation thereof.

What is claimed is:

1. A photoacoustic tomography device comprising:
- a laser positioned to produce acoustic waves in a sample;
- a transducer having a receiving aperture;
- a slit formed by one or more blades positioned substantially parallel to the receiving aperture of the transducer, the slit configured to diffract acoustic waves received by the receiving aperture by way of the slit, wherein a width of the slit is 0.5 to 2.0 times a central acoustic wavelength of the transducer; and
- a processor, in electronic communication with the laser and the transducer, configured to acquire data and reconstruct photoacoustic tomographic images based on the acquired data.

2. The device of claim 1, further comprising:
- a container and a medium dispersed within the container; and
- a sample support;
- wherein the one or more blades are positioned within the medium; and
- wherein the sample support is adjustable such that the sample can be positioned within a field of view of the transducer.

3. The device of claim 2, wherein the container has an orifice covered with a material impermeable to the medium, the material configured to allow acoustic transmission to the transducer.

4. The device of claim 1, wherein the transducer is a linear array transducer.

5. The device of claim 1, wherein the slit is formed by a first blade and a second blade of the one or more blades, the first blade and the second blade being positioned substantially parallel to the receiving aperture of the transducer, such that the slit is formed between the first blade and second blade.

6. The device of claim 5, wherein the first blade and the second blade are substantially parallel to each other.

7. The device of claim 5, wherein the slit is at an acoustic focus of the transducer.

8. The device of claim 5, wherein the first blade has a proximal end in relation to an end of the second blade and the proximal end of the first blade and the end of the second blade are adjustable.

9. The device of claim 8, wherein the proximal end of the first blade and the end of the second blade are independently adjustable.

10. The device of claim 9, wherein the proximal end of the first blade and the end of the second blade are capable of forming or closing the slit.

11. The device of claim 9, wherein the device further comprises a translation stage attached to the first blade or the second blade; and a motion controller in electronic communication with the translation stage.

12. The device of claim 1, wherein the width of the slit is 0.5 to 1.0 times a central acoustic wavelength of the transducer.

13. The device of claim 1, wherein the one or more blades comprise a material having an acoustic impedance at least two times greater than an acoustic impedance of water.

14. The device of claim 1, wherein the laser is a pulsed laser.

15. The device of claim 1, wherein the one or more blades are affixed to the transducer.

16. The device of claim 1, further comprising an acoustic absorber affixed to each of the one or more blades along a surface, of the one more blades, that is proximal to the transducer.

17. A method for performing photoacoustic tomography imaging comprising:
- providing a sample;
- applying a laser to the sample such that the sample produces acoustic waves;
- diffracting the acoustic waves using a slit formed by one or more blades positioned substantially parallel to a receiving aperture of a transducer, wherein a width of the slit is 0.5 to 2.0 times a central acoustic wavelength of the transducer;
- receiving, at the transducer, the diffracted acoustic waves;
- storing, in an electronic memory in electronic communication with the transducer, acoustic data of the acoustic waves; and
- generating an image based on the stored acoustic data.

18. The method of claim 17, wherein the step of receiving acoustic waves is triggered by the application of the laser to the sample.

19. The method of claim 17, wherein the slit is formed between a first blade of the one or more blades substantially parallel to a receiving aperture of the transducer and a second blade of the one or more blades substantially parallel to a receiving aperture of the transducer and at least one of the first blade or second blade is adjustable, the method further comprising the steps of:
- adjusting the first blade or second blade to close the slit; and
- generating a reference reading.

20. The method of claim 17, wherein the transducer comprises a plurality of transducer elements, and the step of generating an image comprises:
- receiving, at a processor, the stored acoustic data;
- setting, using the processor, reconstruction parameters;
- defining, using the processor, a reconstruction area, reconstruction position, and pixel size;
- calculating, using the processor, an acoustic travelling path for the sample to each transducer element; and
- saving, using the processor, each calculated acoustic travelling path into a three-dimensional array.

21. The method of claim 20, wherein the reconstruction parameters comprise slit position, speed of sound, and wavelength.

* * * * *